United States Patent [19]

Kao et al.

[11] Patent Number: 5,783,627
[45] Date of Patent: Jul. 21, 1998

[54] DENSE GAS-COMPATIBLE ENZYMES

[75] Inventors: Fu-jung Kao, Dracut, Mass.; Kenneth E. Laintz, Los Alamos, N. Mex.; Samuel P. Sawan, Tyngsborough, Mass.; L. Dale Sivils, Jupiter, Fla.; W. Dale Spall, Los Alamos, N. Mex.

[73] Assignee: University of Massachusetts, Boston, Mass.

[21] Appl. No.: 709,651

[22] Filed: Sep. 9, 1996

[51] Int. Cl.$^6$ .............................. C12N 9/96; C12N 11/02
[52] U.S. Cl. .................. 525/54.1; 530/402; 530/409; 530/410; 530/811; 530/812; 435/176; 435/177; 435/188
[58] Field of Search .................. 525/54.1; 550/402, 550/409, 410, 811, 812; 435/176, 177, 188

[56] References Cited

U.S. PATENT DOCUMENTS

| | | | |
|---|---|---|---|
| 4,849,357 | 7/1989 | Chung et al. | 435/188 |
| 4,925,790 | 5/1990 | Blanch et al. | 435/52 |
| 4,990,601 | 2/1991 | Skjak-Braek et al. | 536/3 |
| 5,158,704 | 10/1992 | Fulton et al. | 252/309 |
| 5,266,205 | 11/1993 | Fulton et al. | 210/639 |
| 5,467,492 | 11/1995 | Chao et al. | 8/159 |
| 5,478,910 | 12/1995 | Russell et al. | 528/274 |

OTHER PUBLICATIONS

Aaltonen et al., "Biocatalysis in Supercritical $CO_2$", *Chemtech*, 240–248, (1991).

Buckmann et al., "Functionalization of Poly(ethylene Glycol) . . . —(Poly(ethylene glycol)", *Makromol. Chem.* 182:1379–1384 (1981).

Jarzebski et al., "Potentials and Prospects . . . Fluid Technology in Bioprocessing" *Process Biochemistry*, 30:343–352, (1995).

Dordick, "Designing Enzymes for Use in Organic Solvents" *Biotechnol. Prog.* 8:259–267, 1992.

Emerging Technologies Symposium in Hazardous Waste Management, Meeting Announcement, C&EN, Aug. 12, 1996, pp. 45–46.

*Primary Examiner*—Nathan M. Nutter
*Attorney, Agent, or Firm*—Fish & Richardson P.C.

[57] ABSTRACT

An enzymatic reaction system including a modified enzyme, and a dense gas system; modified enzymes; and methods of reacting modified enzymes in a dense gas system or liquid carbon dioxide.

21 Claims, 4 Drawing Sheets

DENSE GAS-COMPATIBLE ENZYMES

STATEMENT AS TO FEDERALLY SPONSORED RESEARCH

Funding for the research described herein was provided, in part, by Los Alamos National Laboratory, Project # 06-6604. The U.S. Federal government may have certain rights in the invention.

BACKGROUND OF THE INVENTION

The invention relates to enzymes modified for use in fluid systems, such as dense gas systems and liquid carbon dioxide.

Unmodified enzymes, in free solution or immobilized on a support, have been used to catalyze certain reactions in supercritical fluids such as supercritical carbon dioxide (Blanch et al. U.S. Pat. No. 4,925,790). Unmodified, solid-enzyme reactions in supercritical fluids are also known (Russell, U.S. Pat. No. 5,478,910).

To improve activity in conventional organic solvents, enzymes have been modified by site-specific mutagenesis to increase enzyme thermostability, increase polarity in the active site, and increase hydrophobicity of a subsite (J. S. Dordick, Biotechnol. Prog. 3:259–267 (1992)).

The syntheses of a variety of poly(ethylene glycol) derivatives are described in A. F. Bückmann and M. Morr, Makromol. Chem. 182:1379–1384 (1981). Bückmann states that enzymes have been rendered nonimmunogenic by linking them to poly(ethylene glycol).

SUMMARY OF THE INVENTION

In general, the invention features an enzymatic reaction system including a dense gas system and a modified enzyme. The modified enzyme includes an enzyme, and a hydrophobic or amphiphilic arm linked to the enzyme. The compatibility of the modified enzyme with a dense gas system is greater than the compatibility of the unmodified enzyme with the dense gas system. The increased compatibility allows the enzymatic reactions to occur at meaningful levels of activity in a dense gas system, instead of in aqueous environments, or in conventional organic solvents.

The dense gas system can include a halocarbon gas (e.g., a $C_{1-5}$ fluorocarbon, a chlorocarbon, or a fluorochlorocarbon gas), a $C_{1-4}$ alkane gas, a $C_{2-4}$ alkene gas, a $C_{2-4}$ alkyne gas, or, preferably, nitrogen gas, carbon dioxide gas or sulfur hexafluoride gas, or a combination of two or more of these gases. The dense gas system can also include a modifier selected from water, $C_{1-6}$ alkanols, $C_{1-6}$ thiols, and $C_{1-6}$ amines, or other additives. The dense gas system can be at various temperatures and pressures, e.g., can be or include a supercritical fluid or a subcritical fluid.

In addition to a dense gas system, the enzymatic reaction system also includes a modified enzyme. A modified enzyme includes an enzyme (e.g., a lipase, a protease, or a cellulase) and one or a plurality of hydrophobic or amphiphilic arms. The arm is linked to the enzyme, e.g., to a side chain of an amino acid of the enzyme, an N-terminus of the enzyme, or a C-terminus of the enzyme. The arm can be linked to the enzyme via an ionic bond or a covalent bond, e.g., via an amide, an ester, a carbamate, a urea, a thiourea, an imide, an amine, a thioester, a thioether, or an ether link.

Hydrophobic arms include halogenated polyesters or halogenated acrylates. Halogenated organic moieties preferably have three or more halogen atoms, i.e., Br, I, and preferably F or Cl. The arm can also be amphiphilic, such as a monomer or polymer selected from polyalkylene glycols, phospholipids, and fatty acids, and surfactants.

A "dense gas system" is a system including one or more gases of low molecular weight (i.e., having a molecular weight less than 150 atomic mass units, "amu") at a pressure greater than atmospheric pressure (14 psi, pounds per square inch, or 0 psig, pounds per square inch gauge). Dense gases include supercritical fluids. Supercritical fluids exist above a critical temperature $T_c$ and critical pressure $P_c$, conditions under which the substance cannot exist as both a gas and a liquid. In general, the viscosity of a supercritical fluid is much lower than a conventional liquid solvent, while the diffusivity of a solute in a supercritical fluid is enhanced. Mass-transfer properties, and thus reaction rates, are generally increased in supercritical fluids.

As used herein, the term "compatibility" as used in "compatibility with a dense gas system" includes partial or complete solubility in the dense gas system, partial or complete wetting by the dense gas system, and the ability of the modified enzyme to interact with the dense gas system, thereby increasing the mass transfer of reactants and products of the enzyme reaction. Compatibility can be indirectly measured by the enzyme specific activity (units/mg protein) in a dense gas system, wherein the calculation for "mg protein" does not include the weight of the arms in the calculation of molecular weight of the protein (see Examples 5 and 6). According to the invention, linking one or more arms to an enzyme increases the compatibility of the now-modified enzyme with the dense gas system.

An "enzyme" can be naturally-occurring or synthetic. An "enzyme" can be obtained by organic synthetic methods, peptide synthetic methods, or recombinant synthetic methods (e.g., enzymes having altered amino acid sequences to improve enzymatic activity). In some embodiments, an "enzyme" is one or more fragments of the native enzyme, which fragments constitute the active site of the native enzyme.

An "arm" is an organic moiety that is amphiphilic or, preferably, hydrophobic. An arm is itself "compatible" with a dense gas system. An arm can be a hydrophobic or amphiphilic organic moiety, which is straight chain or branched, and substituted or unsubstituted, such as $C_{1-25}$ alkyl, $C_{2-25}$ alkenyl, $C_{2-25}$ alkynyl, $C_{1-25}$ acyl, $C_{1-25}$ alkoxy, $C_{6-25}$ alkaryl, $C_{6-25}$ aralkyl, $C_{2-15}$ heteroaryl or $C_{2-15}$ heterocyclic. Substitutions include one or more of F, Cl, Br, I, amino, cyano, isocyanato, imino, carboxyl, hydroxyl, thiol, oxy, thio, and haloacyl, and protected forms thereof. An arm can be a monomer (a relatively low molecular weight material that can polymerize), or a polymer (e.g., a copolymer, or a block copolymer).

The term "linked to an enzyme" means directly or indirectly connected to the enzyme, e.g., to a side chain of an amino acid of the enzyme, or to an N- or C-terminus of the enzyme. The link must be stable in a dense gas system, and should not unduly interfere with the structural stability of the enzyme. The link between an arm and the enzyme can include an ionic, covalent, or noncovalent bond.

An arm can be directly linked to an enzyme by, for example, an amide, an ester, a carbamate, a urea, a thiourea, an imide, an amine, a thioester, a thioether, or an ether link. The nature of the link is not critical to the invention, and is therefore determined by the nature of the arm and by convenience, including commercial availability, efficiency, and purifiable yield. A link can be formed directly by a reaction between a functional group on an enzyme (e.g., amino) and a functional group on an arm (e.g., chloro), such as the reaction between an amino group and a chloroalkyl, to form a covalent bond between the nitrogen on an enzyme and the carbon on the alkyl arm. In this case, the arm is directly linked to an enzyme by a secondary amine moiety. An arm can also be directly linked to an enzyme via an ionic bond between a charged functional group on the enzyme and a oppositely charged functional group on the arm.

An arm can be indirectly linked to an enzyme via a connecting moiety which is linked to both the enzyme and one or more arms. Although an arm is characterized by its compatibility with a dense gas system, a connecting moiety is preferably, but not necessarily, compatible with the dense gas system. The compatibility of the arm or arms linked to the enzyme can compensate for a slightly incompatible character of a connecting moiety.

Like the link between the enzyme and the arm, the nature of the connecting moiety is not critical to the invention, and is determined again by the nature of the functional groups available on the enzyme and on the arm, and factors such as convenience, purifiable yield, and cost. Connecting moieties can include divalent hydrocarbon moieties such as alkylenes, alkenylenes, divalent aryl groups, divalent arylalkyl groups, and divalent alkylaryl groups. These are optionally substituted or functionalized with one or more of the following: fluoro, chloro, amino, hydroxyl, thiol, isocyanato, a double bond, and a triple bond. The unsaturated bond(s) may be conjugated or unconjugated, and of cis, trans, E or Z geometry.

Another aspect of the invention features methods of reacting a modified enzyme in a dense gas system. One method includes mixing a modified enzyme, as described herein, and a substrate (and any necessary cofactors) in a dense gas system. The mixture of the modified enzyme, the substrate, cofactors, and the dense gas system can be heterogeneous or homogeneous. The method can further include separating a reaction product of the modified enzyme from the reaction mixture. The dense gas system is as described herein. For example, the dense gas system can be a supercritical fluid or a subcritical fluid.

The term "mixing" or "mixture" includes homogeneous and heterogeneous combinations of modified enzymes, substrate, and cofactors, if any, in a dense gas system. For example, the mixture may be a true solution, wherein both the enzyme and substrate are dissolved. In addition, the mixture may be a suspension or emulsion, wherein either the enzyme or the substrate are particulate or otherwise not dissolved (such as a substrate "stain" immobilized on an item, e.g., a textile or garment to be cleaned). Mixing includes mechanical mixing, hydrodynamic mixing, flowing a dense gas containing the modified enzyme over an immobilized substrate, flowing a dense gas containing the substrate over an immobilized modified enzyme of the invention, and any other method that results in contacting the modified enzyme with the substrate in an environment containing a dense gas to allow the enzyme to act on the substrate. Any necessary cofactors are also present.

Yet another aspect of the invention is a method of reacting a modified enzyme in liquid carbon dioxide. This method includes mixing a modified enzyme and a substrate (and any necessary cofactors) in liquid carbon dioxide. The modified enzyme is as described elsewhere. For example, the enzyme can be a protease, a lipase, or a cellulase. In one embodiment, the substrate is within a protein stain, a lipid, or a cellulose, e.g., in a stain. In another embodiment, the temperature of the liquid carbon dioxide is between 10° C. and 31° C., and the pressure of the liquid carbon dioxide is between 200 psig and 1000 psig.

The another aspect of the invention also provides methods of modifying an enzyme. One method includes linking a hydrophobic arm to a C-terminus of the enzyme, to an N-terminus of the enzyme, or preferably, to a side chain of an amino acid of the enzyme. In another aspect, the invention provides a modified enzyme, as described in the enzymatic reaction system, e.g., an enzyme linked to a hydrophobic arm.

The enzymatic reaction system, modified enzymes, and the methods of the invention provide numerous advantages. First, replacement of organic solvents with dense gas systems minimizes generation of hazardous wastes. Second by varying temperature and pressure conditions, the density and viscosity of the dense gas or liquid can be manipulated, increasing mass transfer rates, and thereby controlling the reaction rate of the enzyme. Third, changes in density and viscosity of the dense gas system also permit simple separation of combinations of reactants and products based on their solubility. The use of dense gas systems as solvents permits removal or isolation of products without loss of yield or damage to products or enzymes associated with high temperature distillation of organic solvents or the lengthy, chromatographic separation procedures of aqueous reactions. Dense gas systems therefore improve the recovery of, and prolong the life of, the modified enzyme.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the preferred methods and materials are described below. All publications, patent applications, patents, and other references mentioned herein are incorporated by reference in their entirety. In case of conflict, the present specification, including definitions, will control. In addition, the materials, methods, and examples are illustrative only, and not intended to be limiting.

Other features and advantages of the invention will be apparent from the following detailed description, and from the claims.

DETAILED DESCRIPTION OF THE INVENTION

In general, the invention features an enzymatic reaction system including a dense gas system, and an enzyme modified to have improved enzymatic compatibility in the dense gas system. A modified enzyme includes one or more organic arms linked to the enzyme. The arms increase the compatibility of the enzyme with the dense gas system.

Dense Gas System

A dense gas system can include more than one type of gas, wherein each gas is a co-gas in the system. Suitable gases include carbon dioxide, sulfur hexafluoride, freons (e.g., fluoroform, monofluoromethane, dichloromethane, chloroform, chlorotrifluoromethane, and chlorodifluoromethane), $C_{1-4}$ alkanes such as ethane and butane, $C_{2-4}$ alkenes such as ethylene, and $C_{2-4}$ alkynes such as acetylene. In general, a dense gas system should be chemically inert with respect to the enzyme. The dense gas system should not denature the enzyme, or adversely affect its substrate(s), cofactor(s), and products, if any. A dense gas system is a type of fluid system. Fluid systems also include liquid systems such as liquid carbon dioxide or liquid sulfur hexafluoride, discussed below.

Several factors affect the ability of the dense gas system to provide the desired degree of salvation, reaction rate, and other properties for a given substrate or enzyme. These factors include the proportion of the constituent gases in a dense gas system, e.g., the presence of one or more co-gases such as $N_2$ in $CO_2$ (or in hydrocarbons or halocarbons). Temperature and pressure affect the viscosity and density of the dense gas system, and thereby affect reaction rate and mass transfer rates. The temperature of a dense gas system can be between $-70°$ C. and $120°$ C., e.g., between $15°$ C. and $120°$ C. In addition, modifiers such water, $C_{1-6}$ alkanols (e.g., methanol, n-butanol, ethanol, isobutanol, and tert-butanol), $C_{1-6}$ amines, and $C_{1-6}$ thiols can be used, e.g., in small amounts, to adjust the solubility and activity of a modified enzyme.

In one aspect, a dense gas system is preferably a supercritical fluid. Small changes in the temperature and pressure of a supercritical fluid allow separation of combinations of reactants and products, based on solubility.

Enzymes

Enzymes suitable for use in the invention include lipases and proteases, such as those having an E.C. number of 3.1.1.3, Candida cylindracea lipase, subtilisin Carlesberg protease P-5380 (E.C. 3.4.4.16), phospholipase L-3082 and L-3126, Lipozymes (available from Novo Nordisk), Novozyme No. 435, SP-523, SP-525, and SP526. Lipases, proteases, and cellulases are particularly useful for applications related to cleaning, e.g., dry-cleaning in dense gas systems to remove grease or protein-based stains from clothing, and recycling of contaminated plastic waste to break down and separate contaminants (e.g., oil) from the plastic. Organic synthesis or semi-synthetic modifications of a compound can be performed using enzymes modified according to the invention in dense gas systems. In another aspect of the invention, a protein, whether or not an enzyme, is modified for improved compatibility (e.g., solubility) in a dense gas system.

Hydrophobic and Amphiphilic Arms

Arms include low molecular weight hydrophobic and amphiphilic materials. Examples include an acyl group $CH_3(CH_2)_n(C=O)$—, where some H are substituted with halogen (X), such as $CX_3(CX_2)_m(CH_3)_n(C=O)$—, $CX_3(CH_2)_n(CX_3)_m(C=O)$—, cinnamoyl, 2-isopropenoyl $(CH_3—C(=CH_2)—(C=O)$—, and oxiranylmethyl. Arms also include monomers or polymers such as acrylates and polyesters. In one aspect, an enzyme is linked to one or more amphiphilic monomers and polymers such as polyalkylene glycols (e.g., polyethylene glycols, polypropylene glycols), phospholipids, fatty acids, and other surfactants. In general, each arm has a molecular weight between 30 and 5,000 amu, e.g., between 60 and 300 amu. Arms with higher molecular weights, such as those between 4,000 and 10,000 amu, can be used as a comb-shaped arm, with many branches linked to a main chain.

To provide compatibility with a dense gas system, an arm preferably has one or more halogen atoms, e.g., at least 1, 3, 5, 7, or 10 atoms selected from bromine, iodine, chlorine and, preferably, fluorine. Halogenated (e.g., fluorinated) arms therefore include perhalogenated arms, arms with trihalomethyl or pentahaloethyl terminal groups, and haloalkylene groups. Specific examples of arms include 2-N-ethylperfluorooctanesulfonamido ethyl acrylate, 2-N-ethylperfluorooctanesulfonamido ethylmethacrylate, and methoxypolyethylene glycol. An arm can also contain one or more functional groups, such as isocyanato, amino, halocarbonyl (acyl halide), and carboxyl groups.

Where a modified enzyme is linked to a plurality of arms, the arms are independently selected, and may be of varying structure (e.g., substituted, branched, straight, or cyclic), segment molecular weight (e.g., the molecular weight of the monovalent arm, which may reflect structure and number of repeating units), and hydrophobicity. In general, the molecular weight percent of the arm or arms relative to the weight of the enzyme is less than 80%, e.g., less than 50%, or less than 25%, of the molecular weight of the enzyme. The molecular weight of an enzyme, if not available from references or manufacturers, can be calculated by standard techniques, e.g., light scattering or size-exclusion chromatography. The distribution of arms on the enzyme is related to the distribution of the linkage-forming functional groups on the enzyme, as discussed below.

Linking of Arms to Enzymes

In a modified enzyme of the invention, an arm is linked to the enzyme, directly or indirectly, by an ionic bond, a noncovalent interaction or, preferably, a covalent bond. The bond or interaction is formed via the functional groups of the arm and the enzyme. The functional group may be naturally-occurring or artificially added to the enzyme (or arm) by synthetic transformation. In general, the arm is linked to a side chain of an amino acid residue of the enzyme, such as the mercaptomethyl side chain of a cysteine residue, the p-hydroxylbenzyl side chain of a phenylalanine residue, the 4-amino-n-butylene side chain of lysine, or the 3-(propanoic acid) side chain of glutamic acid. The arm can also be linked to an N-terminus or a C-terminus of the enzyme.

Ionic bonds are formed between cationic and anionic functional groups, e.g., carboxylate anions and ammonium cations, on an enzyme, and, respectively, cation- or anion-terminated arms. In contrast to enzymatic reaction methods using polar (e.g., aqueous) media, a dense gas system will not solvate and dissolve ionic linkages.

Covalent links include esters, ethers, thioesters, thioethers, thiourea, carbamate, amine, and amide linkages. In one aspect of the invention, a covalent linkage results from a reaction between a functional group on the side chain of an amino acid of the enzyme (including aromatic rings or double bonds) and a functional group on an arm, with or without a catalyst, crosslinking agent, or activating agent. See Examples 1–4. In another aspect, one or more modified amino acids bearing a side chain already linked to an independently-selected arm of the invention (or with a predetermined, non-natural functional group) are incorporated during the organic, peptide, or recombinant synthesis of an enzyme. In yet another aspect, a non-peptide arm is linked via an amide bond to the backbone of the enzyme, rather than to a side chain of an amino acid of the enzyme. When forming a link between an arm and an enzyme, there can be a connecting moiety between the arm and the terminal functional group which reacts with a functional group on the enzyme to form, e.g., an ester moiety. Similarly, there can be a connecting moiety between the enzyme and the terminal functional group which reacts with a functional group on an arm to form, e.g., an ionic bond.

Non-covalent interactions include hydrogen bonding, van der Waals forces, and chelation, a type of charge interaction.

Modified Enzymes

Modified enzymes can be made in various geometries. Examples include (i) star geometries wherein an enzyme has a plurality of arms radiating from the enzyme, (ii) matrices formed by enzymes which each have a plurality of arms, and that are each cross-linked to one or more enzymes, and (iii) an enzyme linked to a plurality of arms and also linked to a film, a permeable matrix or filter, or other solid support (e.g., a solid or hollow bead). In some cases, enzymatic stability will decrease, and enzymatic compatibility with the dense gas system will increase, as the number or molecular weight percentage of the arm(s) increases. The optimal nature and number of arms for improved enzymatic activity balances solubility on one hand, and conformational stability on the other hand. Enzymatic activity can be determined by methods such as those described in Examples 6 and 7.

The distribution of arms linked to the enzyme is determined by factors such as the number, type, and distribution of functional groups available on the enzyme. Functional groups include those inherent to the natural enzyme, and those made available by one or more synthetic transformations of an inherent functional group. The number and type of functional groups can be controlled by the selective use of protecting groups using standard techniques (see, e.g., PROTECTIVE GROUPS IN ORGANIC SYNTHESIS, edited by T. W. Green and P. G. M. Wuts, 2nd edition, 1991). Conditions which alter the secondary and tertiary structure of the enzyme (e.g., salt, pH, and pressure) can expose different amino acid residues, and in turn, the functional groups on the side chains of those amino acid residues, for preparative manipulation in aqueous or polar aprotic solvents.

Figure 1A:
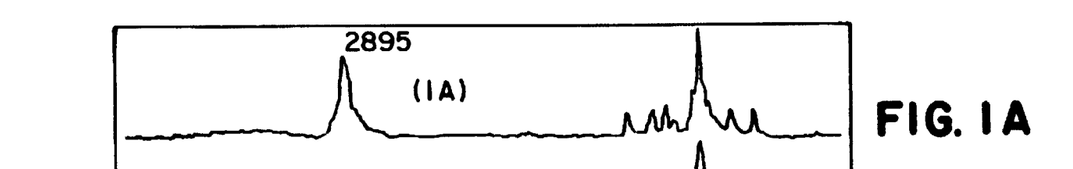
FIGS. 1A to 1C a three comparative FTIR spectra of (1A) methoxy polyethylene glycol, (1B) methoxy polyethylene glycol linked to lipase, and (1C) lipase.
Figure 1B:
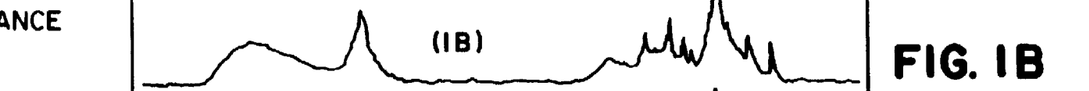
Figure 1C:
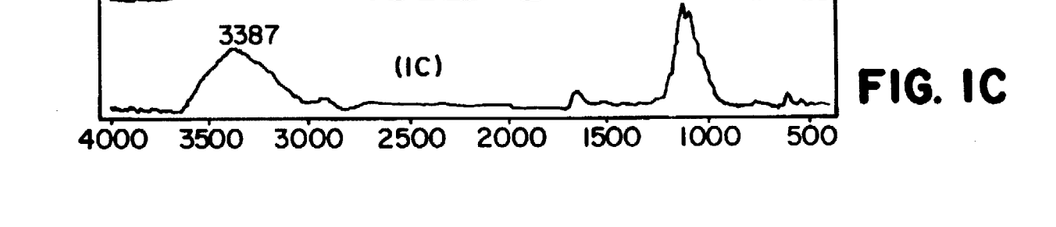
Figure 3:
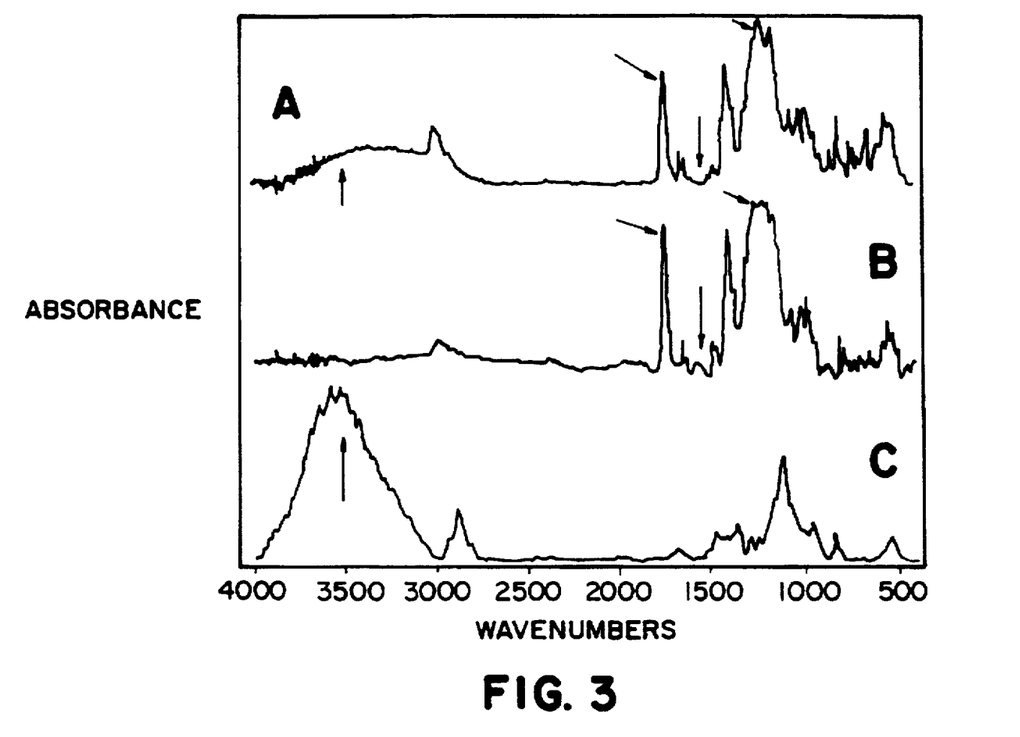
FIGS. 3A to 3C are three comparative FTIR spectra of (3A) fluorinated acrylate linked to lipase, (3B) fluorinated acrylate monomer, and (3C) lipase.

The average number of free functional groups and the average number of arms can be determined by methods known to those in the art, such as a trinitrobenzene sulfonic acid test for free amino groups, or the use of FTIR to monitor the disappearance of a starting material or appearance of a product (see FIGS. 1 and 3). Arms with detectable labels, such as fluorophores or radiolabelled isotopes, can also be used to determine the average number of arms.

An enzyme can be reacted with mixtures of arms having functional groups with different reactivities to produce a random or non-uniform distribution of arms. Reactivity results from factors such as arm length, the linkage-forming functional group on an arm, the stereochemistry of the arm (particularly in the vicinity of the linkage-forming functional group), nature and degree of substitution, and overall conformation.

Arms can be linked to an enzyme by a wide variety of synthetic methods, including condensation (e.g., carbodiimide coupling), nucleophilic substitution, electrophilic substitution, photochemical activation, and photocoupling.

Enzymatic Reaction System

The invention is based, in part, on the discovery that the above-described modified enzymes have improved enzymatic compatibility with a dense gas system, when compared to the compatibility of the unmodified enzyme with e.g., an organic solvent or a dense gas system. The enzymatic reaction system of the invention can be used not only to perform enzymatic reactions, but also, in the absence of a substrate to store the enzyme, to study its structure and other behavior in solution (with or without the substrate in solution or complexed with the enzyme).

As a result of the modifying arms, a modified enzyme of the invention is more compatible, e.g., more soluble, with dense gas systems. Modified enzymes of the invention may have lower enzymatic activities in aqueous media when compared with unmodified enzymes, and the presence of arms may destabilize the structural equilibrium of the enzyme. Nevertheless, in view of the speed with which most enzymes react, and the attractiveness of dense gases as replacements for organic solvents, the increases in solubility are significant. Solubility has been demonstrated by flowing a dense gas over a solid aliquot of enzyme and literally carrying it in solution out of a chamber.

Reactions of Modified Enzymes in Dense Gas Systems

Performing enzymatic reactions in a dense gas system (e.g., dense gases, including sub- or supercritical sulfur hexafluoride, carbon dioxide, haloalkyls, or alkyls) extends the usefulness of enzymes to perform stereo-selective, substrate-selective, and efficient reactions to non-aqueous media. Enzymatic reactions can be synthetic or degradative, and are therefore useful for applications such as pharmaceutical synthesis, dry-cleaning, plastics reclamation, organic synthesis (e.g., stereospecific reactions), and polymer synthesis (e.g., industrial polymers and biopolymers, such as proteins, polysaccharides, and nucleic acids). In addition, dense gas systems, unlike organic solvents, are easier to safely separate from reactants and products, and are more efficiently recycled.

Figure 4:
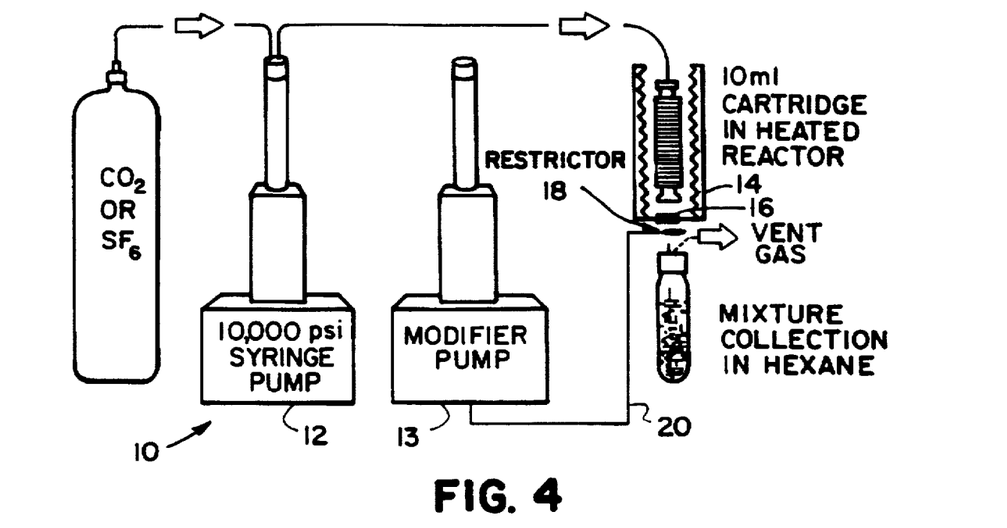
FIG. 4 is a schematic representation of a reactor configuration for high-pressure biocatalytic reactions.

In general, this aspect of the invention features a method of reacting a modified enzyme in a dense gas system by mixing a modified enzyme and a substrate (including any cofactors) in a dense gas system. The modified enzyme contacts and acts on the substrate in the environment of the dense gas system. The reaction product(s), enzyme, and/or substrate can separated from the mixture. One suitable type of reaction apparatus 10 is illustrated in FIG. 4 (ISCO, Lincoln, Nebr.). A supercritical fluid apparatus 10 includes a high-pressure syringe pump 12, a reaction chamber 14, and an outlet 16 connected to a restrictor 18 which allows for the collection of samples. A dense gas passes from pump 12 to reaction chamber 14. Reaction chamber 14 is further connected to a restrictor 18 or a separation instrument which is connected to a means for recycling the dense gas (routed back to the pump) and the enzyme via conduit 20.

There are several methods of obtaining a mixture containing a modified enzyme and a substrate (and any necessary cofactor) in a dense gas system. In one method, a modified enzyme is added to a reaction vessel inside the reaction chamber. Then a solution of an enzyme substrate in a dense gas system at elevated temperature and pressure can be injected into the reaction vessel and allowed to react. In another embodiment, the modified enzyme and substrate in the above example are interchanged.

In a second method, the enzyme and substrate are placed physically apart on adjacent surfaces, e.g., two walls of a vessel. A dense gas system can then be added to the vessel, solubilizing at least one of the modified enzyme and the substrate, and preferably the modified enzyme, thereby allowing a reaction to occur.

For the above reactions, a modified enzyme may be free in solution, in an emulsion, or immobilized on a solid support such as glass beads, polymeric beads, ceramic beads, hollow fibers or tubes, matrices, or hollow vessel surfaces. Similarly, the substrate may be in solution in the dense gas system, or immobilized. Examples of immobilized substrates include an organic molecule linked to a solid support as described above, a proteinaceous or lipid (e.g., grease, oil, or other hydrocarbon or fatty acid) stain on, e.g., fabrics or clothing, and a contaminant in a plastic material. The immobilized organic molecule can be a protein, a nucleic acid, a carbohydrate, or other molecule to be operated upon by a protease, a nuclease or polymerase, a deoxygenase, or other enzyme (kinase, cyclooxygenase, or cellulase), respectively. Homogeneous and heterogeneous reaction systems are therefore possible.

As a result of immobilization, the enzymatic reaction can be a batch reaction using a static, nonagitated autoclave, an agitated autoclave, or an enzyme column with recirculation of the dense gas system and substrate. Alternatively, a semi-batch format has, e.g., a fixed-enzyme bed and a substrate batch with continuous dense gas system flow. Furthermore, a continuous processing format can have, e.g., a fixed enzyme bed used as a "once-through" column. The enzymatic reactions of the invention are suitable for combinatorial syntheses.

In view of the above formats, there are also several methods of separating the product from the enzyme and any unreacted substrate. Separation is straightforward if either the enzyme or the substrate is immobilized. The proportion of enzyme to substrate is usually much les than one.

In general, halogenated arms are compatible with carbon dioxide, sulfur hexafluoride, and halocarbons. Essentially hydrocarbonaceous arms are compatible with carbon dioxide and alkanes.

Reactions of Modified Enzymes in Liquid Carbon Dioxide

The modified enzymes of the invention can also be used in other fluid systems, such as liquid carbon dioxide or liquid sulfur hexafluoride ($SF_6$). A fluid system, like a dense gas system, should be chemically inert with respect to the modified enzyme and any substrate(s) and cofactor(s) of the modified enzyme. Carbon dioxide and sulfur hexafluoride are nontoxic to humans. Based on phase diagrams known to those in the art, the range of temperatures and pressures of the fluid system, e.g., liquid carbon dioxide, can be determined. For carbon dioxide, these are roughly between 15° C. and 31° C., and between 200 psig and 1000 psig. A fluid system can also contain co-fluids and additives, such as those described for dense gas systems.

The following examples are considered illustrative of the principles described above, not limitative.

EXAMPLES

Example 1

Linkage of Methoxypolyethylene Glycol to Lipase

Five reaction mixtures were prepared, each with 200 mg (20.0 μmole) dialyzed lipase dissolved in 50 ml of 0.1M sodium borate (pH 9.2). After cooling each reaction mixture to 4° C., a different amount (0, 5.0, 10.0, 20.0 or 80.0 μmoles) of methoxypolyethylene glycol (PEG, average molecular weight 5,000, from Sigma Chemical Co., St. Louis, Mo.), activated with cyanuric chloride, was added to each mixture. After stirring for 2 hours at 4° C., unreacted PEG was removed by dialysis using a molecular weight cutoff of 8000 Daltons. The modified enzyme was freeze-dried.

Figure 2:
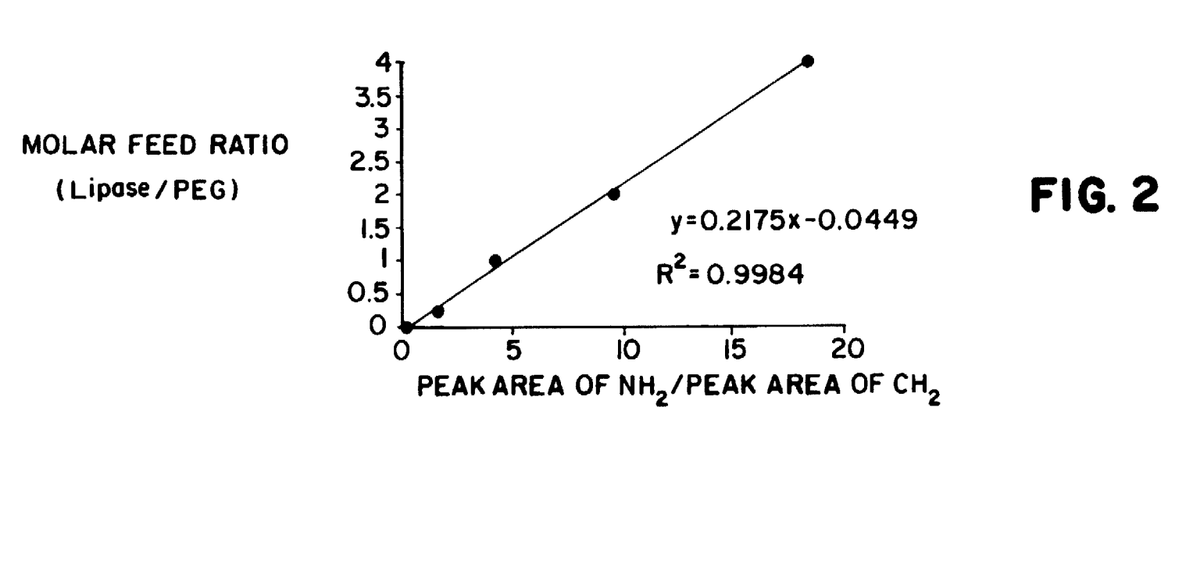
FIG. 2 is a graph of the molar feed ratio of lipase to methoxy polyethylene glycol as a function of the peak area ratio of amino groups (lipase) to methylene (methoxy polyethylene glycol).

The average number of polymer arms linked to the enzyme was calculated using the absorbance ratio of the polymer measured by FTIR spectroscopy (FIGS. 1 and 2)

Example 2

Linkage of Photoinitiator 4,4'-azo-bis(4-Cyanovaleric Acid) to Lipase

Photoinitiator 4,4'-azobis(4-cyanovaleric acid)(ACV) (120 mg) and 80 mg of water-soluble carbodiimide (WSC) (1-ethyl-3-(3-dimethylaminopropyl)carbodiimide hydrochloride) were mixed in a 100 ml buffered solution (pH 7.4). After stirring the mixture for 2 hours at 4° C., lipase (100 mg) was added. The reaction mixture was stirred for 24 hours at 4° C. Unreacted ACV and WSC were removed by dialysis using a molecular weight cutoff of 8000 Daltons. The ACV-modified lipase was freeze-dried and stored at −10° C.

Example 3

Emulsion Polymerization of 2-N-Ethylperfluorooctanesulfonamido Ethyl Acrylate and ACV-Modified Lipase In Examples 3 and 4, respectively, Florad™ fluorochemical acrylate, FX-13 (2-N-ethylperfluorooctanesulfonamido ethyl acrylate), and the methacrylate derivative FX-14 are available from 3M, St. Paul, Minn. The modified enzyme lipase-ACV-(FX-13) was made with FX-13 (0.017 mmoles), polyvinyl alcohol ($1.0 \times 10^{-5}$ mmoles), deionized water (1.3 mmoles), acetone (0.15 mmoles), lipase-ACV ($1 \times 10^{-5}$ mmoles), n-octyl mercaptan ($3.4 \times 10^{-4}$ mmoles). Due to the solubility characteristics of FX-13 and FX-14 (hydrophobic) and lipases-ACV (hydrophilic), a water-miscible organic solvent was used as an additive in emulsion polymerization. All of the reactants except the lipase-ACV were added to a flask under nitrogen and stirred until substantially in solution for 2 hours. The lipase-ACV, dissolved in 2.0 ml of deionized water, was added. The solution was irradiated with a mercury lamp (120 W) for 10 minutes, and then freeze-dried.

The average number of grafted polymer arms was calculated using UV-Vis to measure disappearance of FX-13 monomer concentration before and after the reaction (FIG. 3).

Example 4

Emulsion Polymerization of 2-N-Ethylperfluorooctane-Sulfonamido Ethyl Methacrylate and ACV-Modified Lipase The corresponding FX-14 derivative was prepared as in Example 3 with the substitution of 0.17 mmoles FX-14 for the FX-13. The average number of arms linked to the enzyme was calculated using UV-Vis to measure the decrease in concentration of the FX-14 monomer before and after the reaction.

Example 5

Enzymatic Activity in Hexane

Ester syntheses were carried out in a dark, capped glass vial containing oleic acid (250 mM), ethanol (750 mM), lipase (1.0 μM), and 5% water in 10 ml hexane. It was determined that 250 mM oleic acid and 750 mM ethanol remain completely in solution under the 1200 psi and 50° C. The reaction mixture was incubated at 50° C. with magnetic stirring. Concentration of the ester product was determined by HPLC at various intervals.

The preparation of a standard curve of ethyl oleate in hexane was measured at room temperature using HPLC.

Different concentrations of ethyl oleate were injected with a HP1050 pumping system with an LKB 2140 photodiode array rapid spectral detector using Wavescan™ software on a Bondapack C18 reverse-phase column (3.9 mm×300 mm). Elution was conducted at room temperature with acetonitrile/water (80/20, v/v) and a flow rate of 1.0 ml/min. The detection wavelength was 210 nm. Under these conditions, the retention times for oleic acid and ethyl oleate were 5.7 minutes and 13.7 minutes, respectively. The enzyme activity was reported as μM of ethyl oleate $\text{min}^{-1}$ $\text{mg}^{-1}$ enzyme. The lipase activities in hexane for native lipase, lipase with 0% PEG (dialyzed and freeze dried but not modified), 2.5% PEG, 10% PEG, 20% PEG, and 40% PEG were 20, 2.8, 0.1, 0, 0, and 0, respectively. The lipase activities of FX-13 modified enzyme and FX-14 modified enzyme in hexane were 1.4 and 0.4, respectively.

Example 6

Enzyme Activity in Two Dense Gas Systems

The enzyme activity in supercritical $CO_2$ and $SF_6$ was determined with a high pressure reactor having a high pressure chamber with a volume of 10.0 ml, as shown in FIG. 4 (ISCO SFX™ 220 supercritical fluid extraction system, ISCO Inc.). The pressure and temperature of supercritical $CO_2$ and $SF_6$ were set at 1200 psi and 50° C. respectively, as a compromise between supercritical conditions for $CO_2$ ($T_c$=32° C. and $P_c$=1070 psi) and $SF_6$ ($T_c$=46° C. and $P_c$=546 psi). The temperature was set at 50° C. since n-hexane has a boiling point of 69° C. The final products of the esterification were collected with 10 ml hexane after certain interval of reaction time. The enzyme activity was reported as μM of ethyl oleate $\text{min}^{-1}$ $\text{mg}^{-1}$ enzyme.

The lipase activities in supercritical $CO_2$ for native lipase, lipase with 0% PEG, 2.5% PEG, 10% PEG, 20% PEG, and 40% PEG were 1600, 3.7, 4.7, 0.3, 0, and 0, respectively. The lipase activities of FX-13 modified enzyme and FX-14 modified enzyme were 1.6 and 0.4, respectively. The lipase activities in supercritical $SF_6$ for native lipase, lipase with 0% PEG, 2.5% PEG, 10% PEG, 20% PEG, and 40% PEG were 5700, 11.0, 3.4, 0.9, 0 and 0, respectively. The lipase activities of FX-13 modified enzyme and FX-14 modified enzyme in supercritical $CO_2$ were 1.6 and 0.4, respectively. The lipase activities of FX-13 modified enzyme and FX-14 modified enzyme in supercritical $SF_6$ were 4.5 and 1.5, respectively.

Figure 5:
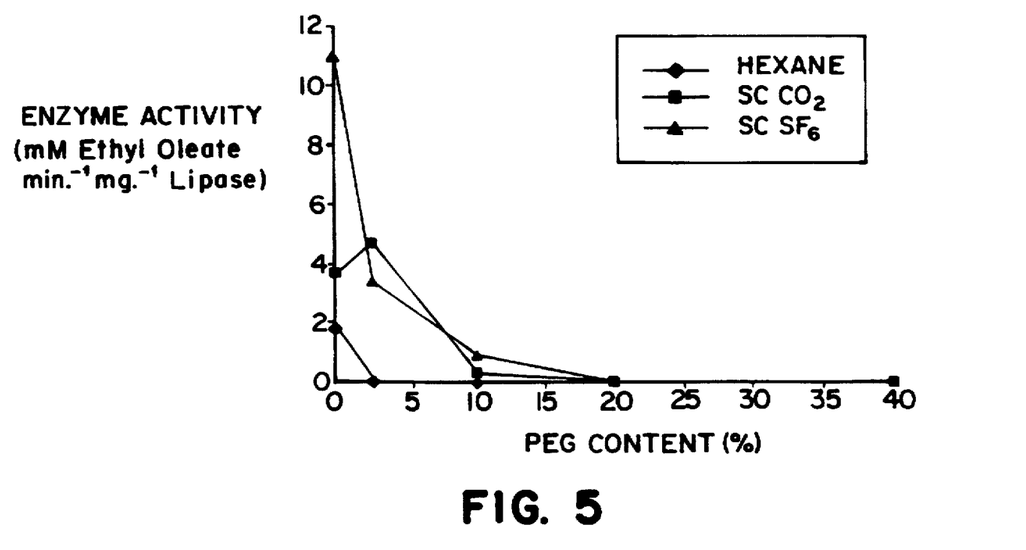
FIG. 5 is a graph of enzymatic activity of modified lipase as a function of methoxy polyethylene glycol content in hexane, supercritical carbon dioxide, and supercritical sulfur hexafluoride.
Figure 6:
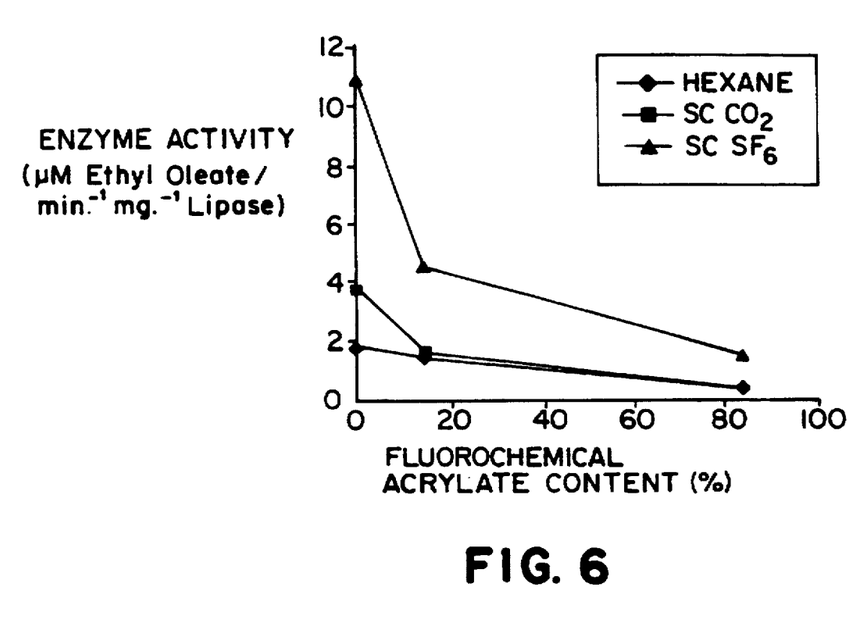
FIG. 6 is a graph of enzymatic activity of modified lipase as a function of fluorinated acrylate content in hexane, supercritical carbon dioxide, and supercritical sulfur hexafluoride.

The modified enzyme and the unmodified enzyme showed higher activity in supercritical fluids than in hexane (see FIGS. 5 and 6). Carbon dioxide may dissolve in the hydration layer associated with the enzyme, thereby lowering the local pH. Alternatively, the carbon dioxide may form covalent carbamate complexes with free amino groups on the surface of the enzyme.

Example 7

Linking an Arm to an Enzyme with Carbodiimide Coupling

Carbodiimide coupling chemistry can be used to link an arm to a nucleophilic functional groups on an arm such as carboxyl, sulfhydryl, phenolic, and, preferably, amino groups. To illustrate, an amino-terminated polymer arm is dissolved in acetonitrile or acetonitrile/water. A carbodiimide such as dicyclohexyl carbodiimide is added to the polymer arm solution. After stirring for at least 30 minutes, the enzyme (e.g., lipase) is added and allowed to react with stirring for an additional 1 to 2 hours. The modified enzyme is separated from the reaction by dialysis against a buffer using a 10,000 MW exclusion membrane. Dialysis is performed for a minimum of 48 hours with 3 changes of the buffer solution. After dialysis, the solution is lyophilized to obtain the modified enzyme in dried form.

Example 8

Linking an Arm to an Enzyme by Condensation Reactions

Polymer arms with reactive functional groups, whether end groups or side groups, will react with the functional groups on a protein to form a covalent bond. To illustrate, an enzyme is dissolved in acetonitrile and water to form a homogeneous solution. Over a period of about an hour, a solution of a polymeric arm terminated with an isocyanate group in acetonitrile is added dropwise to the enzyme solution with stirring. After stirring overnight, the modified enzyme is separated from the reaction mixture by first filtering to remove undissolved solids. The filtrate is dialyzed or run through size exclusion chromatography (SEC). If SEC is used, the filtrate is loaded onto an appropriate column which separates the molecular weights of the modified and native enzyme. The eluent is monitored by a technique such as UV absorbance to allow for the selection of the appropriate element (peak) representing the modified enzyme. Lyophilization of the solution yields the dry, modified enzyme. Activity of the enzyme can be determined by methods such as those in Examples 5 and 6.

Example 9

Linking an Arm to an Enzyme with Photocoupling

A photoreactive group can be linked to an enzyme-modifying reagent (which results in an arm), or the enzyme itself. For example, cinnamic esters of the enzyme and the enzyme-modifying reagent can be used to prepare modified enzymes for use in dense gas systems.

First, an arm is derivatized to contain the ester of cinnamic acid, by reacting cinnamoyl chloride with an arm bearing an amino functional group, such as an amino-terminated arm. The cinnamic acid-terminated arm is isolated using standard techniques such as dialysis, and liquid chromatography. The cinnamic acid derivative retains a vinyl group which is available for a photo-induced coupling reaction. Similarly, the enzyme is derivatized with a photoreactive reagent, such as cinnamoyl chloride.

Second, the photoreactive enzyme derivative is dissolved in acetonitrile/water, preferably in a quartz reaction vessel. A solution of the photoreactive arm derivative in acetonitrile/water is added dropwise to the enzyme derivative solution with vigorous stirring. During dropwise addition, the reaction mixture is irradiated with ultraviolet light which induces the photochemical coupling of the cinnamic acid residues on each of the enzyme and the arm. The coupling yields a cyclobutyl covalent linkage between the enzyme and the arm. Separation of the desired modified enzyme from the reaction mixture, which may contain cyclobutyl-linked arm dimers, is performed by standard techniques such as dialysis and size-exclusion chromatography. The modified protein is isolated, and lyophilized.

Example 10

Templating an Enzyme

An enzyme was first dialyzed against an suitable buffer system to insure maximum activity, i.e., to provide the optimal environment for the enzyme to adopt its active conformation. For example, lipase was dialyzed against pH 7.3 phosphate buffer using a dialysis tubing of 5,000 MW cutoff which promotes formation of the active conformer. After dialysis, the enzyme was stored overnight in the buffer in a dark vial at 4° C., then lyophilized for three days to obtain dry, templated enzyme, i.e., an enzyme as its active conformer. Subsequent manipulations of the conformer in organic solvents, e.g., adding arms or manipulating functional groups, will not alter the conformation.

After templating the enzyme, a crosslinking agent (e.g., glutaraldehyde) can be added to a solution of the conformer in a dense gas or organic solvent. The crosslinking agent will react with functional groups on the active conformer to produce a lightly crosslinked protein in its active state. This protein is now covalently stabilized to allow exposure to water without loss of conformation. Difunctional ionic crosslinking agents may be added in a dense gas system, since the dense gas will not solvate the ionic bond.

Alternatively, a substrate and cofactor, if any, can be added to the dialysis solution. A complex of the enzyme and its substrate is templated, as above. Exposure to an organic solvent or dense gas under conditions which allow the enzyme to act on the substrate, will remove the substrate from the active site.

Use

The modified enzymes of the invention can be used in methods of the invention for applications such as drycleaning, degreasing, precision cleaning, enzyme storage, enzymatic reactions, organic synthesis, metabolism, de-inking, and enzyme-facilitated extractions and separations.

OTHER EMBODIMENTS

It is to be understood that while the invention has been described in conjunction with the detailed description thereof, that the foregoing description is intended to illustrate and not limit the scope of the invention, which is defined by the scope of the appended claims. Other aspects, advantages, and modifications are within the scope of the following claims.

What is claimed is:

1. A modified enzyme having increased compatibility with a dense gas system, comprising
    an enzyme; and
    a hydrophobic arm linked covalently to the enzyme, wherein the compatibility of said modified enzyme with a dense gas system is greater than the compatibility of the unmodified enzyme with said dense gas system.

2. A modified enzyme of claim 1, wherein said hydrophobic arm is linked to a side chain of an amino acid of said enzyme, an N-terminus of said enzyme, or a C-terminus of said enzyme.

3. A modified enzyme of claim 1, wherein the enzyme comprises a plurality of hydrophobic arms, each arm linked independently and covalently to said enzyme.

4. A modified enzyme of claim 1, wherein said arm comprises a fluorine or chlorine atom.

5. A modified enzyme of claim 1, wherein said arm comprises at least three halogen atoms.

6. A modified enzyme of claim 1, wherein said arm is linked to said enzyme via a covalent bond.

7. A modified enzyme of claim 1, wherein said arm is linked to said enzyme via an amide, an ester, a carbamate, a urea, a thiourea, an imide, an amine, a thioester, a thioether, or an ether link.

8. A modified enzyme of claim 1, wherein said arm is a halogenated monomer or halogenated polymer.

9. A modified enzyme of claim 1, wherein said arm is linked to said enzyme via an ionic bond.

10. A modified enzyme of claim 1, wherein said enzyme is a lipase, a protease, or a cellulase.

11. A modified enzyme of claim 1, wherein the hydrophobic arm comprises a halogenated acrylate.

12. A modified enzyme of claim 1, wherein the hydrophobic arm comprises a halogenated polyester.

13. A modified enzyme of claim 1, wherein the hydrophobic arm comprises a polyalkylene glycol.

14. A modified enzyme of claim 1, wherein the hydrophobic arm comprises a polyester.

15. A modified enzyme of claim 1, wherein the hydrophobic arm comprises an acrylate.

16. A modified enzyme of claim 1, wherein the hydrophobic arm comprises a $C_{1-25}$ alkyl, $C_{2-25}$ alkenyl, $C_{2-25}$ alkynyl, $C_{1-25}$ acyl, $C_{1-25}$ alkoxy, $C_{6-25}$ alkaryl, $C_{6-25}$ aralkyl, $C_{2-25}$ heteroaryl, or $C_{2-25}$ heterocyclic moiety.

17. A modified enzyme of claim 1, wherein the hydrophobic arm comprises a $C_{1-25}$ alkyl moiety.

18. A modified enzyme of claim 1, wherein the hydrophobic arm comprises a $C_{2-26}$ alkenyl moiety.

19. A modified enzyme of claim 1, wherein the hydrophobic arm comprises a monomer.

20. A modified enzyme of claim 1, wherein the hydrophobic arm comprises a polymer.

21. A modified enzyme of claim 1, wherein the hydrophobic arm comprises a copolymer.

* * * * *